United States Patent [19]

Karpas et al.

[11] Patent Number: 5,801,144

[45] Date of Patent: Sep. 1, 1998

[54] THE USE OF A COMPOUND FOR THE MANUFACTURE OF A MEDICAMENT FOR THE TREATMENT OF HIV INFECTION

[76] Inventors: Abraham Karpas, 19 Wilberforce Road; Fergal Hill, MRC Centre, Hills Road, both of Cambridge CB2 2OH, England

[21] Appl. No.: 256,952

[22] PCT Filed: Jan. 27, 1993

[86] PCT No.: PCT/GB93/00171

§ 371 Date: May 16, 1995

§ 102(e) Date: May 16, 1995

[87] PCT Pub. No.: WO93/14780

PCT Pub. Date: Aug. 5, 1993

[30] Foreign Application Priority Data

Jan. 28, 1992 [GB] United Kingdom ............... 9201764
Aug. 27, 1992 [GB] United Kingdom ............... 9218223

[51] Int. Cl.$^6$ .............................. A61K 38/00; A61K 31/70
[52] U.S. Cl. .............................................. 514/11; 514/31
[58] Field of Search ................................... 514/11, 31

[56] References Cited

PUBLICATIONS

Douvas et al, 1791, PNAS, vol. 88 pp. 6328–6332.
Shirak, et al 117CA:14436 t 1992.
Wainberg et al 110CA:50931 g 1989.
Klatzman et al 106CA:27522 R 1987.

*Primary Examiner*—Russell Travers
*Attorney, Agent, or Firm*—Cushman Darby & Cushman IP Group of Pillsbury Madison & Sutro

[57] ABSTRACT

Calcineurin antagonists are disclosed for use in the treatment of HIV infection. Preferred materials include cyclosporin A and FK 506.

1 Claim, 5 Drawing Sheets

FIG 1

| Compound | Dosage (μg/ml) | Estimated cell growth in % | Estimated anti-HIV activity in % |
|---|---|---|---|
| Cyclosporin | 10 | 90 | 90 |
|  | 1 | 100 | 70 |
|  | 0.1 | 100 | 20 |
| FK506 | 10 | 50 | 100 |
|  | 1 | 100 | 50 |
|  | 0.1 | 100 | 30 |
| AZT | 10 | Toxic | Toxic |
|  | 1 | 30 | 100 |
|  | 0.1 | 80 | 100 |
|  | 0.001 | 100 | 100 |
|  | 0.0001 | 100 | 100 |

THE USE OF A COMPOUND FOR THE MANUFACTURE OF A MEDICAMENT FOR THE TREATMENT OF HIV INFECTION

DESCRIPTION

The present invention relates to the use of a compound for the manufacture of medicament for the treatment of Human Immunodeficiency Virus (HIV) infection.

Infection by HIV, of which there are two distinct types HIV-1 and HIV-2, leads to the development of Acquired Immune Deficiency Syndrome (AIDS)[1,2]. Several compounds which interfere with the replication of the virus have been developed for the treatment of AIDS, however only one compound, AZT (Azidothymidine), has been widely used in the treatment of HIV infection.

Although AZT is a highly effective drug in blocking HIV replication, it has two major drawbacks. Firstly, it is frequently toxic inhibiting not only HIV replication but also the division of bone marrow cells causing anaemia, leukopenia, neutropenia and thrombocytopenia[3,4]. Secondly, within six months of prolonged treatment, AZT-resistant mutants of HIV appear[5].

Thus, there is an urgent need to find drugs that will interfere with HIV replication without overt cytotoxicity. It is known that HIV replication depends on T-cell activation and proliferation.

The aim of the present invention is to develop an agent which inhibits HIV replication. It was thought that if T-cell activation could be suppressed, HIV replication would be inhibited.

This aim is achieved by affecting the signal transduction pathway for T-cell activation by administering calcineurin-antagonists and/or rotamase-antagonists and/or NF-AT-antagonists.

Accordingly the present invention provides the use of calcineurin-antagonists for the manufacture of a medicament for the treatment of HIV infection.

In another aspect, the present invention provides the use of rotamase-antagonists for the manufacture of a medicament for the treatment of HIV infection.

In a further aspect, the present invention provides the use of NF-AT-antagonists for the manufacture of a medicament for the treatment of HIV infection.

Suitable for use according to the present invention are compounds that act as calcineurin-antagonists, rotamase-antagonists or NF-AT-antagonists, for example
Cyclosporin A (Cyclo {-[4-(E)-but-2-enyl-N, 4-dimethyl-L-threonyl]-L-homoalanyl-(N-methylglycyl)-(N-methyl-L-leucyl)-L-valyl-(N-methyl-L-leucyl)-L-alanyl-D-alanyl-(N-methyl-L-leucyl)-(N-methyl-L-leucyl)-(N-methyl-L-valyl)}) and
FK506 (16-Allyl-1, 14-dihydroxy-12-[2-(4-hydroxy-3-methoxycyclohexyl)-1-methylvinyl]-23,25-dimethoxy-13, 19,21,27-tetramethyl-11,28-dioxa-4-azatricyclo-[22,3,1,0$^{4,9}$]octacos-18-ene-2,3,10,16-tetrone)

Also included within the scope of the invention are medicaments for the treatment of HIV infection which comprise a compound of the invention as active ingredient in association with a pharmaceutically acceptable carrier or diluent.

The medicament of the invention will normally be administered orally or by injection.

Compositions for parenteral administration will normally be solutions in aqueous saline, which is pyrogen free for human use. Such compositions can be administered intravenously or intraperitoneally.

Compositions for oral administration will mostly be in solid or liquid form, mostly as tablets, capsules, lozenges, etc. Liquid compositions can be solutions or dispersions in aqueous or non-aqueous media. Ideal solutions are of neutral or alkaline pH and of low ionic strength, e.g 5% dextrose.

Suitable daily doses of the antagonists when used in accordance with the invention range from about 10 mg to 1 g/m$^2$ body surface.

BRIEF DESCRIPTION OF THE DRAWINGS

FIG. 1: Cytotoxicity and anti-HIV activity of the drugs.

The following Examples illustrate the present invention:

EXAMPLES

Example 1

Assay for the Effect of Cyclosporin A (CsA) and FK506 on HIV Cell Fusion and Replication Method: A clone of the leukaemia T-cell line Molt 4, which expresses a very high level of CD4, was selected. This was infected with the highly cytopathic NDK strain of HIV-1[6] and a clone which is chronically infected with the virus but which readily replicates was selected. When these HIV-infected cells w ere co-cultivated with non-infected Molt 4 cells at a ratio of 100 non-infected:1 infected cell, very large giant cells were formed within 24 hours.

The formation of giant cells in the mixed culture was used as a rapid assay to determine the anti-HIV effect of CsA and FK506. The effects of serum from healthy HIV-1 infected individuals and AIDS patients on giant cell formation was also examined. In addition the level of cytotoxicity and anti-HIV-1 activity of these substances was tested in an anti-HIV assay system which has been previously described[7]. This enabled us to establish the anti-viral activity and cytotoxicity in parallel and to compare it to the effects of AZT on virus inhibition and cell division.

Results: 1. Giant Cell Assay: When various cells cultures were examined after 24 hours the cells which were co-cultivated with chronically infected cells contained a high proportion of very large and pleomorphic giant cell formations. In contrast, when the same cells were co-cultured in the presence of 10 μg/ml of CsA or FK506, only a few small giant cells could be observed. When chronically infected cells, cultured for one week in the presence of the drugs, were washed and then co-cultivated with non-infected cells in the absence of the drug, a few small giant cells could be seen during the first 24 hours. However after prolonged culture larger giant cells were formed.

2. HIV Inhibition: The effect of various concentrations of CsA and FK as well as AZT on HIV-1 replication are outlined in FIG. 1. Although AZT is known to be toxic in vivo, it appears to be a far more effective drug in blocking replication of the virus.

Example 2

Effect of Cyclosporin A and FK506 on the Growth-Rate of Non-infected and Chronically Infected T-Cells Method: Molt 4 cells and the clone of the same cells, chronically infected with HIV-1, were seeded separately at an approximate concentration of $5 \times 10^4$ cells/ml. Five separate cultures of each of the two cell populations were seeded. One was grown with growth medium alone, the others with 4 μg/ml of CsA, 10 μg/ml of CsA, 4 μg/ml of FK and 10 μg/ml of FK. At 24 hour intervals samples were taken for cell counting. Feeding with or without the corresponding chemical was done after the fourth day. AZT was also used in parallel.

Figure 2A:
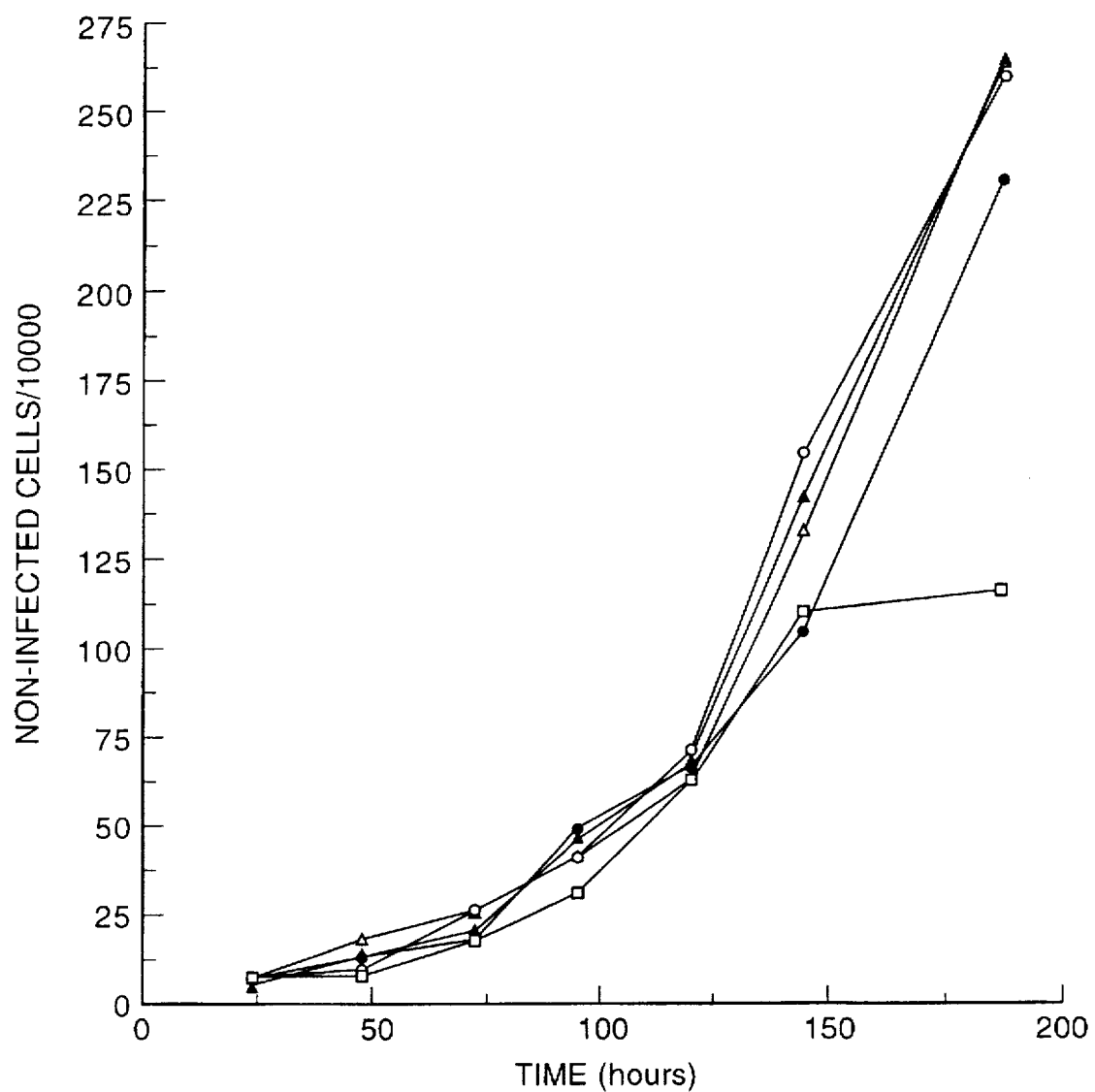
FIG. 2A: Effect of the drugs on the growth of non-infected cells. Open triangle, control cells grown in the presence of growth medium only; closed triangle, cells grown in the presence of 4 μg/ml CsA; open circle, cells grown in the presence of 10 μg/ml CsA; closed circle, cells grown in the presence of 4 μg/ml FK506; and, open square, cells grown in the presence of 10 μg/ml FK506.

Results: FIG. 2a shows that CsA did not reduce the rate of T-cell division, either at a concentration of 10 or 4 μg/ml, when compared to cells which were grown in the presence of growth medium alone. Likewise, for the first five days FK did not affect the growth of uninfected cells. Thereafter there was only a marginal increase in the number of cells in the presence of 10 μg/ml FK while 4 μg/ml, did not appear to slow cell division.

Figure 2B:
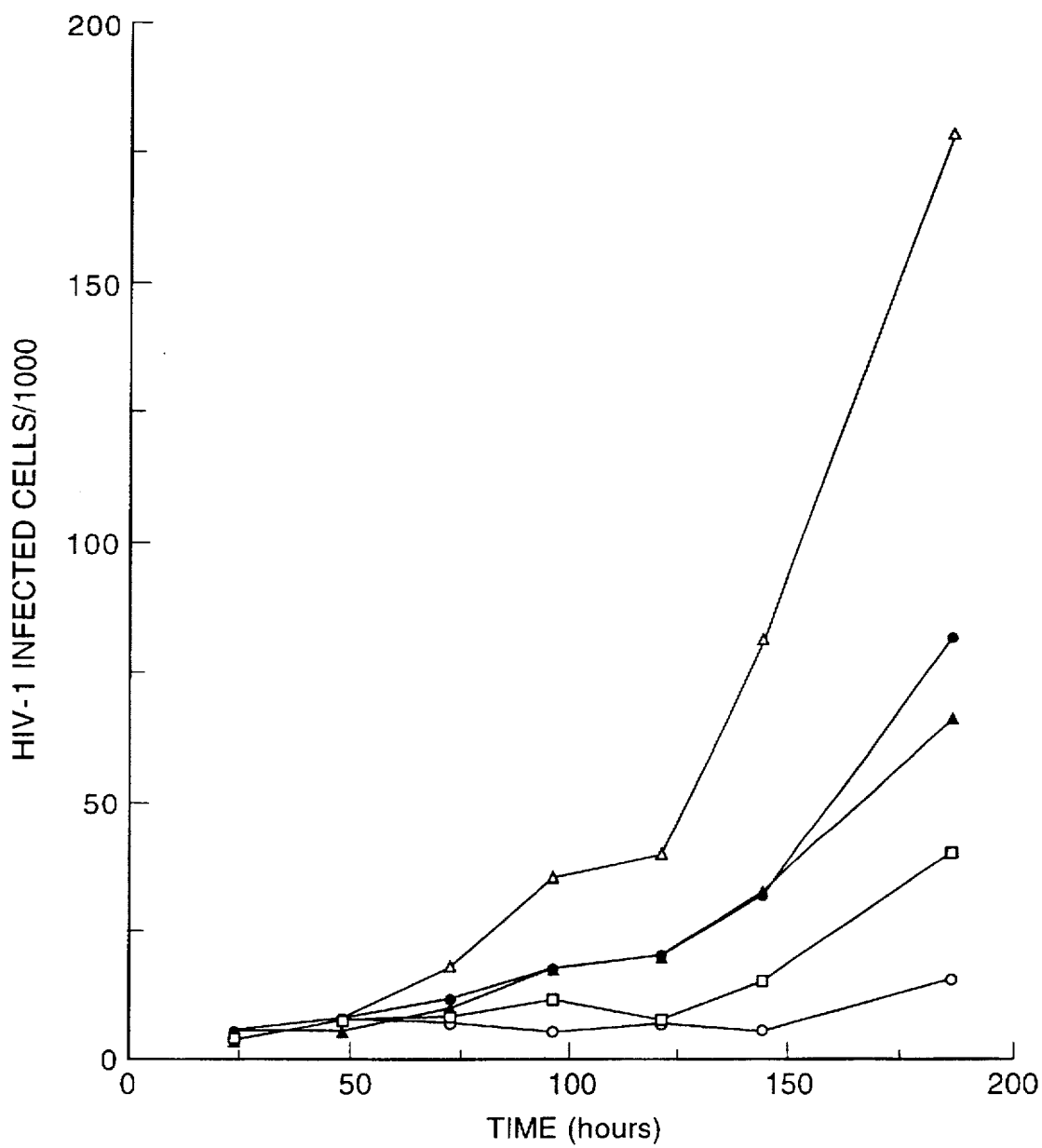
FIG. 2B: Effect of the drugs on the growth of chronically infected cells. Open triangle, control cells grown in the presence of growth medium only; closed triangle, cells grown in the presence of 4 μg/ml CsA; open circle, cells grown in the presence of 10 μg/ml CsA; closed circle, cells grown in the presence of 4 μg/ml FK506; and, open square, cells grown in the presence of 10 μg/ml FK506.

Most interesting was the effect of the two drugs on the same T cells chronically infected with HIV-1. FIG. 2b shows that both drugs significantly inhibited the replication of the HIV-1 infected cells. At a concentration of 10 μg/ml there was only a marginal increase in the number of cells after a week in culture. With a lower concentration of 4 μg/ml there was still a significant reduction in cell division. Unlike CsA and FK, AZT was toxic to the chronically infected cells as it was to the uninfected cells.

Example 3

Effect of Cyclosporin A and FK506 on CD4 Expression

Figure 3:
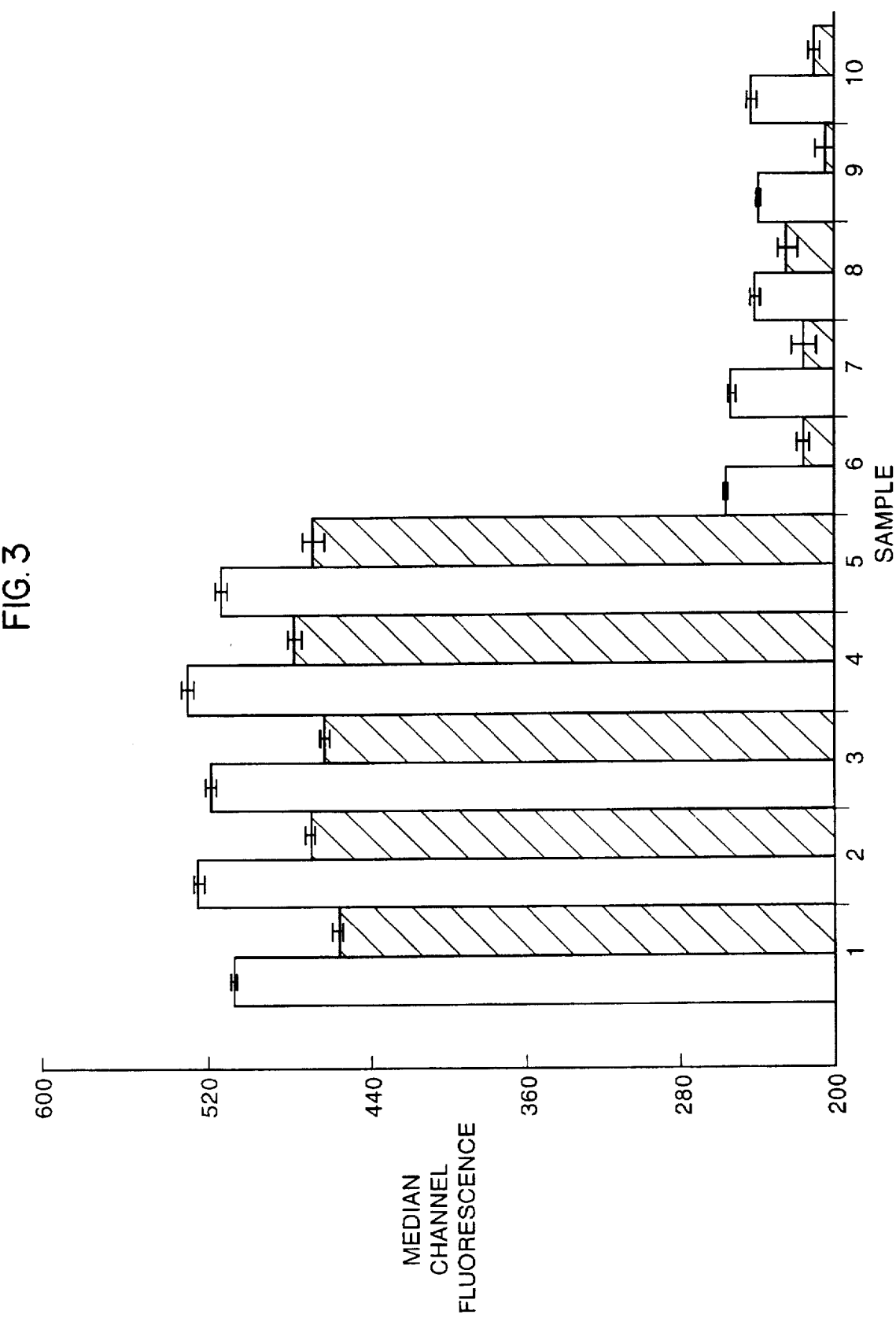
FIG. 3: Effect of cyclosporin A and FK506 on CD4 expression. Samples 1–5 were non-infected cells 1) in growth medium only, 2) with 1 μg/ml CsA, 3) with 4 μg/ml CsA, 4) with 1 μg/ml FK506, and 5) with 4 μg/ml FK506. Samples 6–10 were HIV-1 chronically infected cells 6) in growth medium only, 7) with 1 μg/ml CsA, 8) with 4 μg/ml CsA, 9) with 1 μg/ml FK506, and 10) with 4 μg/ml FK506. Leu 3a/3b OKT4a monoclonal antibodies. Bars indicate mean on three replicates with error bars.

Method: Both the non-infected Molt 4 cells as well as the HIV-1 chronically infected cells were grown in the presence of CsA and FK506. Each cell preparation was kept separately at a concentration of 1 and 4 μg/ml of each drug for 3 days. Infected and uninfected cells were suspended at a concentration of $10^6$/ml in phosphate buffered saline (PBS) containing 0.1% sodium azide. Triplicate aliquots of 100 μl were incubated separately with 20 μl Leu-3a (FITC) (Ortho (Becton Dickinson UK Ltd) or with 10 μl OKT4a (FITC) Diagnostic Systems). After 20 min at 22° C. the cells were washed twice with PBS and resuspended in 0.51% paraformaldehyde/PBS (Sigma). The preparations were fixed overnight at 4° C. and subsequently analysed by flow cytometry (FACScan, Becton Dickinson UK Ltd). The median channel fluorescence was recorded for each sample. Results: FIG. 3 shows that uninfected Molt 4 cells expressed a high level of CD4 even when grown in the presence of 1 and 4 μg/ml of CsA or FK. In contrast, FIG. 3 also shows that the chronically HIV-1 infected Molt 4 cells expressed a very low level of CD4 which does not seem to be affected by either CsA or FK.

Example 4

Production of Infectious HIV

Method: Culture fluid was collected from:

1. chronically infected cells grown in growth medium;
2. chronically infected cells grown in 10 μg/ml of CsA for a week and for a week after removal of the compound;
3. chronically infected cells grown in 10 μg/ml of FK506 and for 1 week after removal of compound;

Each culture was titrated at serial ten-fold dilutions. Each dilution was used to infect Molt 4 cells in duplicate. The end point was recorded after 10 days.

Figure 4:
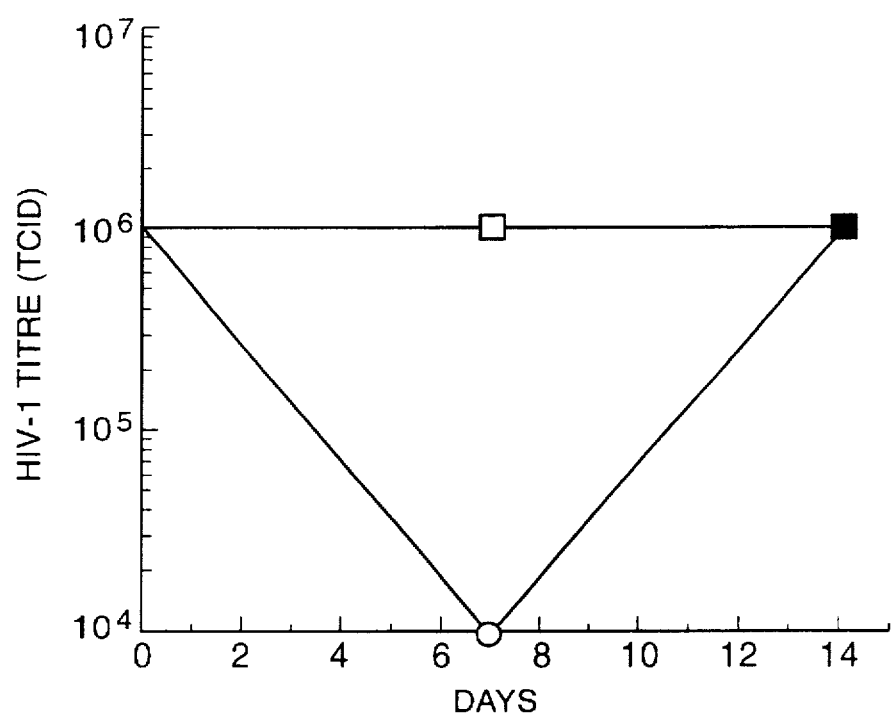
FIG. 4: Effect of the drugs on the release of infectious HIV particles from chronically infected cells. Open square, tissue culture infected dose (TCID) released from the infected cells in the presence of growth medium; open circle, TCID released from the infected cells when grown in either 10 μg/ml CsA or FK506; and, closed square, TCID released for a week after the drugs were removed.

Results: FIG. 4 shows that approximately $10^6$ infectious HIV particles per ml can be recovered from the culture fluid of chronically infected cells. However, when the cell cultures were assayed for infectious particles after one week of growth in the presence of CsA or FK506 there was about 100-fold drop in the yield of infectious HIV in both culture fluids. When the drug-containing culture medium was replaced with growth medium alone, there was a recovery in the rate of cell division with an increase in the production of infectious HIV-1 to the levels which preceded the drug treatment.

Example 5

Electron Microscopy

Method: Cloned Molt 4 cells, chronically infected with HIV-1 NDK, and the same cells grown for 5 days in the presence of CsA were fixed in 3% glutaraldehyde. Ultrathin sections of cytoplasm were examined for the presence of budding virus particles in CsA treated and untreated cells.

Results: Systematic electron microscopic examination of the chronically HIV-1 infected cells revealed that most ultrathin sections contained readily recognisable and morphologically distinctive virus particles. In contrast most of the sections from the cultures which were grown in the presence of CsA were devoid of detectable virus particles: the frequency of viral detection was lower than 1 in 50 cell sections and only a few particles could be seen.

Discussion

The experiments demonstrate an inhibition of and a delay in the onset of cytopathic effects, in particular giant cell formation, on co-cultivation of uninfected cells with chronically infected cells which had been grown in the presence of either drug for five days and then washed (FIG. 1). In addition, using the anti-HIV assay system previously developed [7], we were able to detect marginal antiviral activity at non-toxic concentrations. The inhibition of HIV-1 replication by either CsA or FK506 was, however, far lower than that of AZT. Furthermore at 1 μg CsA and/or FK506 there was only a partial decrease in HIV-1 replication.

The effect of both drugs on the expression of CD4 was studied. As can be seen in FIG. 3, concentrations of 1 and 4 μg/mg CsA caused no reduction in the expression of CD4 on the surface of the non-infected cells.

The experiments also demonstrate that during acute infection, when uninfected cells were co-cultivated with infected cells in the presence of the drugs, both CsA and FK506 had anti-HIV-1 and anti-HIV-2 activity within 24 hours, as shown in the delay of the cytopathic effect (FIG. 1). The drugs were not found to inhibit or slow down the replication of the uninfected leukaemia T-cells (FIG. 2a). By contrast, both drugs inhibited the replication of the cells chronically infected with HIV-1 (FIG. 2b). With AZT the inhibitory effect on growth did not discriminate between infected or non-infected T-cells. It is not known why Cyclosporin A and FK506 should inhibit the replication of HIV-1 infected cells at concentrations which do not inhibit uninfected cells. Nevertheless it is not unreasonable to suppose that the same phenomenon may also occur in vivo in HIV-infected individuals.

The mechanism of inhibition of HIV production by these drugs is thought to be threefold:

1) through the inhibition of synthesis of active NF-AT, an important transcription factor in activated T-cells[8]. No active NF-AT is found in resting T-cells but it is produced in response to antigen recognition and signal transduction by the T-cell receptor complex. Since the productive replication of HIV depends on activated T-cells, the inhibition of NF-AT production could explain the significant reduction of HIV synthesis. Our chronically infected cells, which grew in the presence of the drugs, produced only about 1/100th the amount of the infectious particles released by non-treated cells into the culture fluid. Likewise, electron microscopic examination of ultrathin sections of cells revealed nearly 100-fold reductions in the frequency of distinct HIV particles in cell cultures treated with the drugs. These virological and ultrastructural studies suggest that both drugs also interfere with transcription of the HIV provirus. Staining of the drug-treated cells for HIV-1 antigen was also weaker when compared to non-treated cells.

2) through the inhibition of the cytoplasmic enzyme peptidyl-prolyl cis-transisomerase (rotamase) which facilitates protein folding. It is thought that the formation of a rotamase-drug complex is responsible for the inhibition of HIV replication.

3) through the inhibition of calcineurin, a protein which is present in the cytoplasm of T-cells.

How and why the drugs inhibit the replication of the chronically infected cells at concentrations which do not affect the replication of non-infected cells is not clear.

Summary

In conclusion the effects of the drugs Cyclosporin A and FK506 have been studied on chronically HIV-1 infected cells, as well as on non-infected and newly infected cells. Both drugs were found to inhibit the growth of the chronically infected cells at concentrations which did not inhibit the growth of the non-infected cells. In addition there was approximately at 100-fold reduction in the yield of infectious HIV-1 when the infected cells were grown in the presence of these drugs, a finding consistent with the decrease in HIV expression. When cells chronically infected with HIV-1 or with HIV-2 were co-cultivated with uninfected cells in the presence of CsA or FK506 there was a delay in the formation of giant cells (syncytia) and cytopathic effects (CPE). This inhibitory effect was not due to decrease in the expression of membrane CD4.

The results, demonstrating the inhibition of HIV-1 and 2 production by CsA and FK506, suggest that both drugs could be used to treat HIV-infected individuals. For patients who have already developed HIV associated disease and AIDS, these drugs could be used in combination with passive immunization, an established therapy which has been used in treatment of various conditions over the years[9,10].

REFERENCES

1) Barré-Sinoussi F, Cherman J C, Rey F, Nugeyre M T, Chamaret S, Gruest J, Daugert C, Axler-Blin C, Brun-Vezinet F, Rouzioux C, Rozenbaum W & Montagnier L. (1983) *Science* 220: 868–870.
2) Clavel F, Guetard D, Brun-Vezinet F, Chamaret S, Rey M A, Santos-Ferreira M O, Laurent A G, Dauguet C, Katlama C, Rouzioux C, Klatzman D, Champalimaud J L & Montagnier L. (1986) *Science* 223: 343–346.
3) Dournon E, Matheron S, Rozenbaum W, Gharakhanian S, Michon G, Girard P M, Perron N E, Salmon D, Detruchi S P, Leport C, Bouvet E, Dazza M C, Levacher M & Regnier B. (1988) *Lancet* ii: 1297–1302.
4) Mir N & Costello C. (1988) *Lancet* ii: 1195–1196.
5) Larder B & Kemp SD. (1989) *Science* 246: 1155–1158.
6) Ellrodt A, Barre-Sinoussi F, Le Bras P, Nugeyre MT, Brun-Vezinet F, Rouzioux C, Segond P, Caquet R, Montagnier L and Chermann J C. (1984) *Lancet i*: 1383–1385.
7) Karpas A, Fleet G W J, Dwek R, Petursson S, Namgoong S K, Ramsden N G, Jacob G S, Rademacher T. (1988) *PNAS USA* 85: 9229–9233.
8) Flanagan W M, Corthesy B, Bram R J, Crabtree G R. (1991) *Nature* 352: 803–807.
9) Karpas A, Hill F, Youle M, Cullen V, Gray J, Byron N, Hayhoe F G J, Tenant-Flowers M, Howard L, Gilgen D, Oates J K, Hawkins D, Gazzard B. (1988) *PNAS* 85: 9234–9237
10) Karpas A, Hewlett I K, Hill F, Gray J, Byron N, Gilgen D, Bally V, Oates J K, Gazzard B. Epstein J E. (1990) *Proc Natl Acad Sci USA* 87:7613–7617.

We claim:

1. A method of inhibiting the growth of HIV-infected cells which comprises administering thereto an effective amount of FK 506.

* * * * *